(12) United States Patent
Morsi

(10) Patent No.: US 10,028,745 B2
(45) Date of Patent: Jul. 24, 2018

(54) ADVANCED ENDOVASCULAR CLIP AND METHOD OF USING SAME

(75) Inventor: Hesham Morsi, Houston, TX (US)

(73) Assignee: Noha, LLC, Houston, TX (US)

( * ) Notice: Subject to any disclaimer, the term of this patent is extended or adjusted under 35 U.S.C. 154(b) by 303 days.

(21) Appl. No.: 13/154,265

(22) Filed: Jun. 6, 2011

(65) Prior Publication Data

US 2012/0253369 A1  Oct. 4, 2012

Related U.S. Application Data

(60) Provisional application No. 61/516,175, filed on Mar. 30, 2011.

(51) Int. Cl.
| | | |
|---|---|---|
| *A61F 2/02* | (2006.01) | |
| *A61B 17/12* | (2006.01) | |
| *A61B 17/00* | (2006.01) | |

(52) U.S. Cl.
CPC .... *A61B 17/12022* (2013.01); *A61B 17/1215* (2013.01); *A61B 17/12031* (2013.01); *A61B 17/12113* (2013.01); *A61B 17/12172* (2013.01); *A61B 17/12177* (2013.01); *A61B 2017/00867* (2013.01); *A61B 2017/00871* (2013.01); *A61B 2017/00893* (2013.01)

(58) Field of Classification Search
USPC ....... 606/108, 151, 157, 158, 191, 198, 213, 606/215, 216; 623/1.11, 1.13–1.16, 1.18, 623/1.19, 1.23, 1.32, 1.34, 1.42, 623/1.44–1.47, 23.72
See application file for complete search history.

(56) References Cited

U.S. PATENT DOCUMENTS

| | | |
|---|---|---|
| 4,311,146 A | 1/1982 | Wonder |
| 4,341,218 A | 7/1982 | Ü |
| 4,360,023 A | 11/1982 | Sugita et al. |
| 4,364,392 A | 12/1982 | Strother et al. |
| 4,395,806 A | 8/1983 | Wonder et al. |
| 4,484,581 A | 11/1984 | Martin et al. |
| 4,658,822 A | 4/1987 | Kees |

(Continued)

FOREIGN PATENT DOCUMENTS

| | | |
|---|---|---|
| JP | 1-249045 | 10/1989 |
| JP | 2-154748 | 6/1990 |

(Continued)

OTHER PUBLICATIONS

IUPAC. Compendium of Chemical Terminology, 2nd ed. (the "Gold Book"). Compiled by A. D. McNaught and A. Wilkinson. Blackwell Scientific Publications, Oxford (1997).*

(Continued)

*Primary Examiner* — Robert Lynch
(74) *Attorney, Agent, or Firm* — Norton Rose Fulbright US LLP

(57) ABSTRACT

The present disclosure provides an endovascular device for treating a defect in the vascular wall such as aneurysm by deploying a self expandable barrier around the aneurysm neck to block the blood flow to the aneurysm and method for implementing the endovascular device. The endovascular device also allows for delivery of certain swellable materials and bioactive materials, such as thrombogenic compounds, to the aneurysm to accelerate occlusion and healing of the aneurysm.

14 Claims, 10 Drawing Sheets

(56) References Cited

U.S. PATENT DOCUMENTS

| | | |
|---|---|---|
| 4,660,558 A | 4/1987 | Kees, Jr. |
| 4,710,192 A | 12/1987 | Liotta et al. |
| 4,765,335 A | 8/1988 | Schmidt |
| 4,932,955 A | 6/1990 | Merz et al. |
| 4,966,603 A | 10/1990 | Focelle et al. |
| 5,122,136 A | 6/1992 | Guglielmi et al. |
| 5,411,549 A | 5/1995 | Peters |
| 5,423,829 A | 6/1995 | Pham et al. |
| 5,522,823 A | 6/1996 | Kuntz et al. |
| 5,522,836 A | 6/1996 | Palermo |
| 5,540,680 A | 7/1996 | Guglielmi et al. |
| 5,624,449 A | 4/1997 | Pham et al. |
| 5,634,932 A | 6/1997 | Schmidt |
| 5,702,418 A | 12/1997 | Ravenscroft |
| 5,733,294 A | 3/1998 | Forber et al. |
| 5,749,894 A | 5/1998 | Engelson |
| 5,758,420 A | 6/1998 | Schmidt et al. |
| 5,769,816 A | 6/1998 | Barbut et al. |
| 5,776,097 A | 7/1998 | Massoud |
| 5,795,331 A | 8/1998 | Cragg et al. |
| 5,824,059 A | 10/1998 | Wijay |
| 5,855,578 A | 1/1999 | Guglielmi et al. |
| 5,868,783 A | 2/1999 | Tower |
| 5,891,128 A | 4/1999 | Gia et al. |
| 5,895,385 A | 4/1999 | Guglielmi et al. |
| 5,919,187 A | 7/1999 | Guglielmi et al. |
| 5,921,957 A | 7/1999 | Killion et al. |
| 5,925,016 A | 7/1999 | Chornenky et al. |
| 5,925,037 A | 7/1999 | Guglielmi et al. |
| 5,928,226 A | 7/1999 | Guglielmi et al. |
| 5,928,260 A | 7/1999 | Chin et al. |
| 5,935,148 A | 8/1999 | Viller et al. |
| 5,941,888 A | 8/1999 | Wallace et al. |
| 5,941,896 A | 8/1999 | Kerr |
| 5,944,714 A | 8/1999 | Guglielmi et al. |
| 5,947,962 A | 9/1999 | Guglielmi et al. |
| 5,947,963 A | 9/1999 | Guglielmi |
| 5,976,126 A | 11/1999 | Guglielmi |
| 5,976,162 A | 11/1999 | Doan et al. |
| 5,984,929 A | 11/1999 | Bashiri et al. |
| 6,010,498 A | 1/2000 | Guglielmi |
| 6,015,424 A | 1/2000 | Rosenbluth et al. |
| 6,017,977 A | 1/2000 | Evans et al. |
| 6,024,754 A | 2/2000 | Engelson |
| 6,048,333 A | 4/2000 | Lennox et al. |
| 6,051,607 A | 4/2000 | Greff |
| 6,053,941 A | 4/2000 | Lindenberg et al. |
| 6,059,779 A | 5/2000 | Mills |
| 6,066,133 A | 5/2000 | Guglielmi et al. |
| 6,077,260 A | 6/2000 | Wheelock et al. |
| 6,083,220 A | 7/2000 | Guglielmi et al. |
| 6,096,021 A | 8/2000 | Helm et al. |
| 6,123,714 A | 9/2000 | Gia et al. |
| 6,146,396 A | 11/2000 | Konya et al. |
| 6,258,115 B1 | 7/2001 | Dubrul |
| 6,315,787 B1 | 11/2001 | Tsugita et al. |
| 6,342,064 B1* | 1/2002 | Koike ............... A61B 17/0057 606/151 |
| 6,454,780 B1 | 9/2002 | Wallace |
| 6,488,706 B1 | 12/2002 | Solymar |
| 6,585,748 B1 | 7/2003 | Jeffree |
| 6,855,154 B2 | 2/2005 | Hesham |
| 6,878,161 B2 | 4/2005 | Lenker |
| 7,195,636 B2 | 3/2007 | Avellanet et al. |
| 7,367,986 B2 | 5/2008 | Mazzocchi et al. |
| 7,468,072 B2 | 12/2008 | Morsi |
| 7,914,549 B2 | 3/2011 | Morsi |
| 7,993,364 B2 | 8/2011 | Hesham |
| 8,062,379 B2 | 11/2011 | Morsi |
| 8,075,585 B2 | 12/2011 | Lee et al. |
| 8,100,938 B2 | 1/2012 | Figulla et al. |
| 8,292,914 B2 | 10/2012 | Morsi |
| 8,313,505 B2 | 11/2012 | Amplatz et al. |
| 8,372,088 B2 | 2/2013 | Morsi |
| 9,084,589 B2 | 7/2015 | Moszner |
| 2001/0012951 A1 | 8/2001 | Bates et al. |
| 2002/0010481 A1 | 1/2002 | Jayaraman |
| 2002/0038140 A1 | 3/2002 | Yang et al. |
| 2003/0028209 A1 | 2/2003 | Teoh et al. |
| 2003/0028213 A1* | 2/2003 | Thill ............... A61B 17/0057 606/200 |
| 2003/0055455 A1* | 3/2003 | Yang ............... A61B 17/0057 606/215 |
| 2003/0195553 A1 | 10/2003 | Wallace et al. |
| 2005/0043786 A1* | 2/2005 | Chu et al. ............... 623/1.42 |
| 2005/0131443 A1 | 6/2005 | Abdel-Gawwad |
| 2006/0167494 A1 | 7/2006 | Suddaby |
| 2006/0282111 A1 | 12/2006 | Morsi |
| 2007/0106311 A1* | 5/2007 | Wallace et al. ............... 606/151 |
| 2007/0179527 A1* | 8/2007 | Eskuri et al. ............... 606/213 |
| 2008/0200945 A1* | 8/2008 | Amplatz et al. ............... 606/195 |
| 2008/0312684 A1* | 12/2008 | Drasler et al. ............... 606/213 |
| 2009/0210048 A1 | 8/2009 | Amplatz et al. |
| 2011/0213407 A1 | 9/2011 | Morsi |
| 2012/0253369 A1 | 10/2012 | Morsi |
| 2013/0310803 A1 | 11/2013 | Morsi |

FOREIGN PATENT DOCUMENTS

| | | |
|---|---|---|
| JP | 3-060652 | 3/1991 |
| JP | 9-070405 | 3/1997 |
| WO | WO-97/04813 | 2/1997 |
| WO | WO-97/27888 | 8/1997 |
| WO | WO-97/45131 | 12/1997 |
| WO | WO-98/09570 | 3/1998 |

OTHER PUBLICATIONS

Micrus Corporation, "Micrus Microcoil Delivery System", 2001, Micrus Corporation, http://www.micruscorp.com/coils.html, Feb. 15, 2002, p. 1 of 2.

Company News on Call, "NMT Medic. Announces Agreement to Sell Vena Cava Filter Assets", http://www.prnewswire.com, Feb. 15, 2002, p. 1 of 2.

ORCMT, Success Story, "Clinical Neuro Systems", http://orcmt.oakridge.org/success/clinicat.html, Feb. 15, 2002, p. 1 of 2.

Mizuho, "Sugita Aneurysm Clips", http://www.mizuho.com/aclips1.html, Feb. 15, 2002, p. 1 of 1.

Untitled Stacked Page, Press Releases, Aug. 2001: MicroVention Raises $12.5 Million in Late-Stage Financing: Minimally Invasive Technology Attracts Several New Medical Device Investors, http://www.microvent.com, Feb. 15, 2002, p. 1 of 2.

Onyx™ Liquid Embolic System, http://www.microtherapeutics.com/products_onyx.html, Feb. 15, 2002, p. 1 of 3.

K.I. Arnautovic, et al., "A Combined Microsurgical Skull-Base and Endovascular Approach to Giant and Large Paraclinoid Aneurysms", Elsevier Science, Inc., 1998, pp. 504-516.

Yiu-Wah Fan, et al., "Retrograde Suction Decompression of Paraclinoid Aneurysm—A Revised Technique", Elsevier Science, Inc., 1999, pp. 129-131.

T. Schmitz-Rode, et al., Embolotherapy of Aneurysms Under Temporary Balloon Occlusion of the Neck, Investigative Radiology, 1999, pp. 317-321.

Puay-Yong Ng, et al., "Intraoperative Endovascular Treatment as an Adjunct to Microsurgical Clipping of Paraclinoid Aneurysms", J. Neurosurg., vol. 93, Oct. 2000, pp. 554-559.

Office Action in U.S. Appl. No. 12/434,137 dated Dec. 6, 2010, 9 pages.

International Search Report and Written Opinion in foreign proceedings PCT/US2012/030371, dated Jul. 24, 2012, 19 pages.

IUPAC. Compendium of Chemical Terminology, 2nd ed. (the "Gold Book"). Compiled by A.D. McNaught and A. Wilkinson. Blackwell Scientific Publications, Oxford, 1997.

* cited by examiner

ADVANCED ENDOVASCULAR CLIP AND METHOD OF USING SAME

TECHNICAL FIELD

The present invention relates generally to medical devices and methods of using same, and more specifically, to medical devices for treating or treating a defect in the vascular wall, such as an aneurysm.

BACKGROUND OF THE INVENTION

Aneurysms result from weakening of the blood vessel, which causes the wall of the blood vessel to balloon outwardly under the hemodynamic stress of the flowing blood, thereby creating an aneurysm. Aneurysm formation and growth can have serious consequences such as pressure on the adjacent brain or other tissues and nerves and eventual rupture which can be fatal.

Given the life-threatening nature of such intracranial aneurysms, several methods of treating aneurysms have been attempted, with varying degrees of success. For example, open craniotomy is a procedure by which an aneurysm is located, and treated extravascularly. This procedure can have significant disadvantages. For example, it is an open surgery in which the surgeon must typically remove a portion of the patient's skull and violate the brain coverings, and can also traumatize brain tissue in order to reach the aneurysm.

Other known techniques used in treating aneurysms are performed endovascularly. Such techniques typically involve attempting to form a mass within the sac of the aneurysm. For instance, a microcatheter is often used to access the aneurysm, where the distal tip of the micro catheter is placed within the sac of the aneurysm, allowing for deposit of embolic material into the sac of the aneurysm. The embolic material includes, for example, detachable coils or liquid polymer. This approach, however, suffers from various disadvantages. For example, the detachable coils can exert pressure on the inside weak walls of the aneurysm, causing ruptures of the aneurysm with a potentially fatal brain hemorrhage. Additionally, coils can migrate out of the sac of the aneurysm and into the parent artery which can lead to clot formation and stroke. Another drawback is that the detachable coils can compact over time due to the space existing between the coils. Coil compaction can result in recanalization of the aneurysm caused by the continued hemodynamic forces from the blood circulation, which is particularly common in bifurcated aneurysms treated with coils.

In addition to the drawbacks associated with coils, embolic liquid migration is also a problem. For instance, when a liquid polymer is injected into the sac of the aneurysm, it can migrate out of the sac of the aneurysm, which can lead to irreversible occlusion of the parent vessel. Techniques have been developed to minimize the risk of coils and embolic liquid migration into the parent vessel, such as temporary occlusion of the parent vessel at the origin of the aneurysm using a removable balloon. However, these techniques suffer from various disadvantages also. For instance, it is sometimes undesirable to occlude the parent vessel, even temporarily. In addition, the migration prevention techniques may not prevent all embolic material migration into the parent vessel, particularly after the removing of the balloon.

Yet another technique to prevent coils migration involves depositing a permanent stent in the parent vessel across the origin of the aneurysm. This technique, however, often require premedicating the patient with strong blood thinner which can be problematic particularly in the setting of ruptured aneurysm and brain hemorrhage.

Another recent trend in endovascular technique for treating cerebral aneurysms involves permanent insertion of a tightly woven high density stent in the parent vessel across the origin of the aneurysm to divert the blood flow away from the aneurysm. This technique also suffers from the disadvantage of needing strong blood thinner, as well as potential inadvertent occlusion of some of the adjacent normal blood vessel, such as perforators. Such occlusion can lead to a devastating stroke. Moreover, the high density stent also suffers from the disadvantage that it cannot be used to treat bifurcated aneurysms.

In view of the above, there remains a need to develop new devices that effectively and safely treat cerebral aneurysms ruptured and unruptured aneurysms.

BRIEF SUMMARY OF THE INVENTION

The present disclosure provides an endovascular device for treating a defect in the vascular wall such as aneurysm by deploying a self expandable barrier around the aneurysm neck to block the blood flow to the aneurysm. The present disclosure also provides methods for implementing the endovascular device.

According to one aspect of the present disclosure, there is provided an endovascular clip comprising: a first deformable component; a second deformable component; each of said first and second deformable components comprises: a lattice comprising plurality of strands intersecting one another, wherein said intersecting strands form a plurality of interstices; a joint component attached to a portion of each of said first and second deformable components; wherein each of said first and second deformable components comprises a self-expanding material configured to have an original configuration and a deformed configuration; wherein said deformed configuration is generally perpendicular to said original configuration; wherein said self-expanding material is configured to change from said deformed configuration to said original configuration at least by exposure to an activating condition; wherein at least one of said first deformable component and said second deformable component is configured to extend across an opening in a vascular wall in the original configuration. In one embodiment, the opening is a neck of an aneurysm.

In one embodiment, said self-expanding material comprises nitinol. In another embodiment, said activating condition comprises a temperature above a defined threshold. In another embodiment, at least one of said first deformable component and said second deformable component further comprises a frame component, wherein said frame component circumscribes said lattice. In yet another embodiment, the diameter of said frame component is larger than the circumference of a portion of said strands of said lattice.

In another embodiment, at least one of said first deformable component and said second deformable component further comprises a reinforcing component having a first end and a second end, wherein both ends of said reinforcing component are attached to said frame member. In another embodiment, said lattice of at least one of said first deformable component and said second deformable component further comprises a swellable material configured to expand in volume upon exposure to an activating condition. In yet another embodiment, said swellable material is selected from the group consisting of hydrogel, hydrogel foam, hydrophilic polymers with conjugated collagen, hydrophilic polymers without conjugated collagen, porous hydrated polyvinyl alcohol foam (PAF) gel, and any combination thereof.

In another embodiment, said swellable material seals at least a portion of said interstices of the respective deformable component when exposed to the vascular content. In another embodiment, said lattice further comprises a bioactive material configured to promote cell growth. In another embodiment, said bioactive material comprises a thrombogenic material selected from the group consisting of collagen, fibrinogen, vitronectin, other plasma proteins, growth factors, peptides of said growth factors having attached RGD (arginine glycine-aspartic acid) residues, phospholipids, polymers with phosphorylcholine functionality, and any combination thereof.

In another embodiment, a portion of the strands from the lattice of said first deformable component obstructs a plurality of said interstices of said second deformable component. In another embodiment, the diameter of a first plurality of strands of said lattice are larger than the diameter of a second plurality of strands of said lattice. In another embodiment, said second plurality of strands are arranged to aid said change from said deformed configuration to said original configuration. In another embodiment, said second plurality of strands are located near the center of said lattice.

In another embodiment, said joint component is configured to be releasably attached to a delivery wire. In another embodiment, a portion of the vascular wall near the opening is sandwiched between a portion of said first deformable component and a portion if said second deformable component when said first deformable component and said second deformable component are extended across the opening in the vascular wall. In another embodiment, the medical device further includes a radiopaque material. In yet another embodiment, at least one of said first deformable component and said second deformable component has a shape selected from the group consisting of circular, oval, square, rectangular, concave, convex, generally leveled, and any combination thereof. In one embodiment, the endovascular clip further comprises a polymer. In another embodiment, the frame component comprises nitinol and the lattice component comprises a polymer.

According to another aspect of the present disclosure, there is provided an endovascular clip comprising: a first deformable component comprising a first frame component and a first reinforcing component; wherein a portion of said first frame component is attached to a portion of said reinforcing component; a second deformable component comprising a lattice having a plurality of strands intersecting one another, wherein said intersecting strands form a plurality of interstices; a joint component attached to a portion of each of said first and second deformable components; wherein each of said first and second deformable components comprises a self-expanding material configured to have an original configuration and a deformed configuration; wherein said deformed configuration is generally perpendicular to said original configuration; wherein said self-expanding material is configured to change from said deformed configuration to said original configuration at least by exposure to an activating condition; wherein at least one of said first deformable component and said second deformable component is configured to extend across an opening in a vascular wall in the original configuration. In one embodiment, the opening is a neck of an aneurysm.

In one embodiment, said self-expanding material comprises nitinol. In another embodiment, said activating condition comprises a temperature above a defined threshold. In another embodiment, said lattice further comprises a swellable material configured to expand in volume upon exposure to an activating condition. In another embodiment, said swellable material is selected from the group consisting of hydrogel, hydrogel foam, hydrophilic polymers with conjugated collagen, hydrophilic polymers without conjugated collagen, porous hydrated polyvinyl alcohol foam (PAF) gel, and any combination thereof. In another embodiment, said swellable material seals at least a portion of said interstices of the respective deformable component when exposed to the vascular content. In another embodiment, said lattice further comprises a bioactive material configured to promote cell growth. In another embodiment, said bioactive material comprises a thrombogenic material selected from the group consisting of collagen, fibrinogen, vitronectin, other plasma proteins, growth factors, peptides of said growth factors having attached RGD (arginine glycine-aspartic acid) residues, phospholipids, polymers with phosphorylcholine functionality, and any combination thereof. In another embodiment, said joint component is configured to be releasably attached to a delivery wire. In another embodiment, a portion of the vascular wall near the opening is sandwiched between a portion of said first deformable component and a portion if said second deformable component when said first deformable component and said second deformable component are extended across the opening in the vascular wall. In yet another embodiment, the medical device further includes a radiopaque material. In one embodiment, the endovascular clip further comprises a polymer. In another embodiment, the first frame component comprises nitinol and the lattice component comprises a polymer. In another embodiment, the first frame component consists of the first frame component and the first reinforcing component.

According to another aspect of the present disclosure, there is provided a method for treating an aneurysm comprising the steps of: extending a first deformable component of an endovascular clip within an aneurysm across a portion of the neck of said aneurysm; extending a second deformable component of said endovascular clip across a portion of the neck of said aneurysm; wherein each of said first and second deformable components comprises: a lattice comprising plurality of strands intersecting one another, wherein said intersecting strands form a plurality of interstices; wherein a portion of first and second deformable components are attached to a joint component of said endovascular clip; wherein each of said first and second deformable components comprises a self-expanding material configured to have an original configuration and a deformed configuration; wherein said deformed configuration is generally perpendicular to said original configuration; wherein said self-expanding material is configured to change from said deformed configuration to said original configuration at least by exposure to an activating condition; wherein at least one of said first deformable component and said second deformable component is configured to extend across the neck of an aneurysm in the original configuration.

In one embodiment, the method includes the step of delivering a swellable material configured to expand in volume upon exposure to an activating condition to the aneurysm by coating a portion of at least one of said first and second deformable components with said swellable material. In another embodiment, said swellable material is selected from the group consisting of hydrogel, hydrogel foam, hydrophilic polymers with conjugated collagen, hydrophilic polymers without conjugated collagen, porous hydrated polyvinyl alcohol foam (PAF) gel, and any combination thereof.

In another embodiment, the method includes the step of: delivering a bioactive material configured to promote cell growth to said aneurysm by coating a portion of at least one of said first and second deformable components with said bioactive material. In one embodiment, said bioactive material comprises a thrombogenic material selected from the group consisting of collagen, fibrinogen, vitronectin, other plasma proteins, growth factors, peptides of said growth factors having attached RGD (arginine glycine-aspartic acid) residues, phospholipids, polymers with phosphorylcholine functionality, and any combination thereof.

The foregoing has outlined rather broadly the features and technical advantages of the embodiments present disclosure in order that the detailed description of these embodiments that follows may be better understood. Additional features and advantages of the embodiments of the present disclosure will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

The accompanying drawings, which are incorporated in and form a part of the specification, illustrate the embodiments of the present invention and together with the written description serve to explain the principles, characteristics, and features of the invention. In the drawings.

DETAILED DESCRIPTION OF THE INVENTION

Figure 1A:
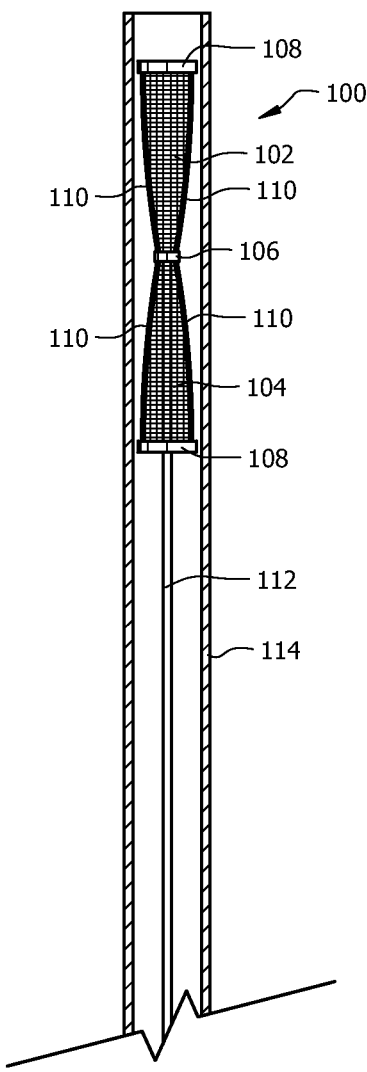
FIG. 1A is a side view of a preferred embodiment of the present disclosure in a collapsed state within a catheter.

The present disclosure provides endovascular therapeutic device and methods for delivering and deploying such devices an within the vasculature of a patient to occlude aneurysms, such as cerebral aneurysms.

Referring to FIGS. 1A-1D, the endovascular clip 100 comprises a distal self-expanding disc or member 102 and a proximal self-expanding disc or member 104. The self-expanding members 102 and 104 are joined to a connecting joint 106. In the preferred embodiment, each of self-expanding members 102 and 104 substantially comprises a single layer of intersecting wires or strands forming a mesh having a plurality of interstices. The strands or wires may comprise a superelastic and/or self-expanding material. In particular, superelastic and/or self-expanding material should have properties that allow it to have a deformed shape under one condition and to recover its original shape prior to deformation upon exposure to an activation mechanism. Preferably, the material can include a memory-shaped heated alloy such as nitinol, or nickel titanium, which is a metal alloy of nickel and titanium. Nitinol alloys exhibit two closely related and unique properties: shape memory and superelasticity. Shape memory refers to the ability of nitinol to undergo deformation at one temperature, then recover its original, un-deformed shape upon heating above its "transformation temperature." That is, nitinol alloy has a biased self expanded condition and may be compressed into a collapsed or deformed condition before use. During use, it may be exposed to temperature above the transformation threshold, thereby causing it to revert back to its un-deformed shape.

In certain embodiments, in addition to self-expanding material, the strands of members 102 and 104 may comprise any desired material or combination of materials, including, but not limited to, a metal, an alloy, a composite, a polymer, and the like. For example, a plurality of strands may comprise nitinol, stainless steel, cobalt chromium, platinum, titanium, plastic, or any combination thereof. The strands may each have a diameter preferably between about 5-200 microns, and more preferably between 40 to 60 microns. In other embodiments, the diameter of the strands are configured to according to the selected size of the endovascular clip 100.

In another embodiment, one or both of the self-expanding discs 102 and 104 can comprise more than one layer of wire mesh. The pattern of the mesh may be regular or irregular, as long as the pattern of the strands of the mesh form a plurality of interstices. For instance, referring to FIGS. 1A and 1B, the strands of the mesh may be perpendicular to one another such that squares or rectangular openings are formed. In other embodiments, circular or irregularly shaped openings may be formed. In one embodiment, the square or rectangular openings may be of uniform dimensions or they may be of different dimensions. For example, the strands closer to the center of the self-expanding disc, e.g., member 102 or 104, may be placed closer to one another to form smaller openings, as compared to larger interstices may be formed by strands placed further apart from one another near the edge of the self-expanding disc, or vice versa. Additional aspects of the density of the strands of the mesh are further discussed below. Preferably, the number and placement of the strands are configured to provide a mesh with a minimum amount of material that is still sufficient to allow the endovascular clip 100 to serve at least as a physical barrier to isolate the aneurysm from the flow of the parent artery. A self-expanding disc with a minimal yet sufficient mesh provides a lighter endovascular clip that allows for better maneuverability when it is being inserted and placed in the patient.

Referring to FIGS. 1A-1E, the mesh can be reinforced by a ring or frame 108 that is attached to the periphery of self-expanding members 102 and 104. The frame 108 can also comprise a superelastic and/or self-expanding material, such as nitinol, or any other material that provides similar superelasticity properties. In particular, referring to FIGS. 1B and 1E, the peripheral frame 108 has a deformed or compressed shape with a smaller diameter in FIG. 1B than the un-deformed, original shape shown in FIG. 1E. The peripheral frame 108 may comprise a single strand that has a larger diameter than the strands of the mesh. In one embodiment, the diameter of the peripheral frame 108 is at least double the diameter of the strands of the mesh of self-expanding discs 102 and 104. In another embodiment, the diameter of peripheral strand 108 is between about 10-500 microns. More preferably, the diameter of the peripheral frame 108 is about 80-120 microns. The peripheral frame 108 can have different un-deformed shapes such as circular, oval, rectangular or any other regular or irregular shapes that may be suitable to the application, e.g., appropriate fit with the neck of a particular aneurysm or diameter of a particular opening in the vascular wall.

Figure 1B:
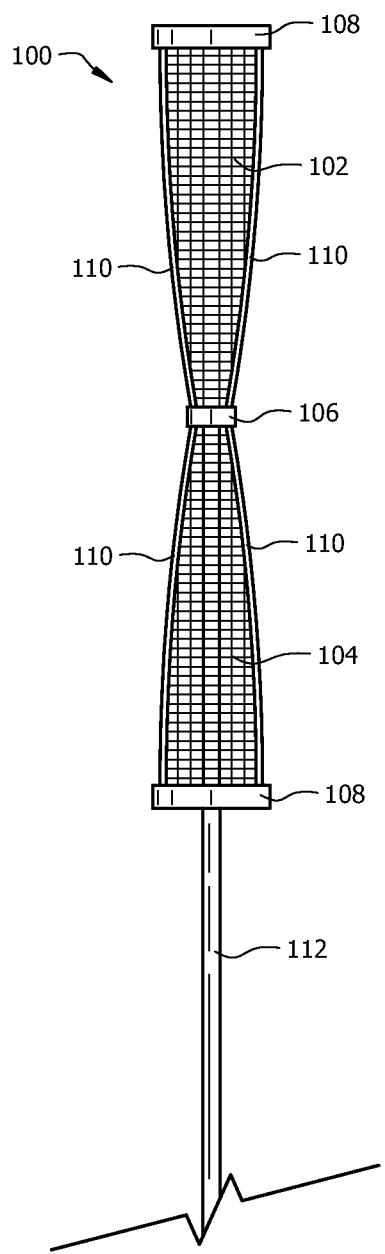
FIG. 1B is a side view of the preferred embodiment of the present disclosure in a collapsed state.
Figure 1C:
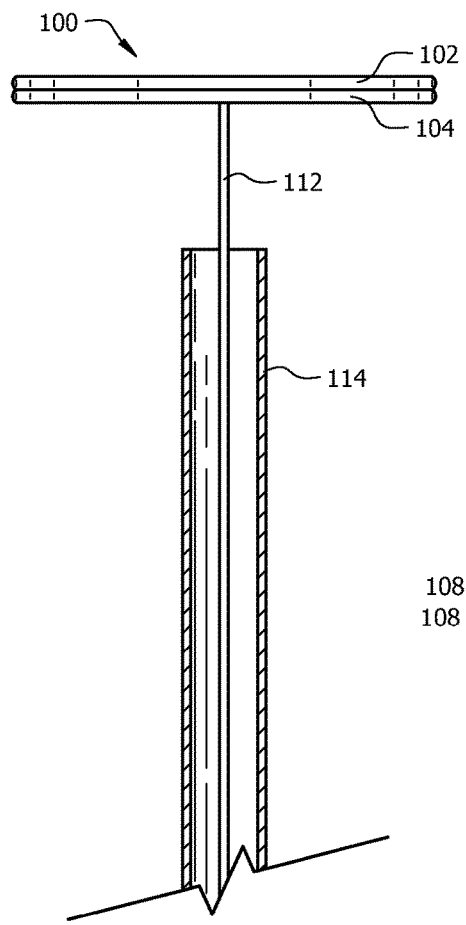
FIG. 1C is a side view of the preferred embodiment of the present disclosure in a non-collapsed state and attached to a delivery wire.
Figure 1D:
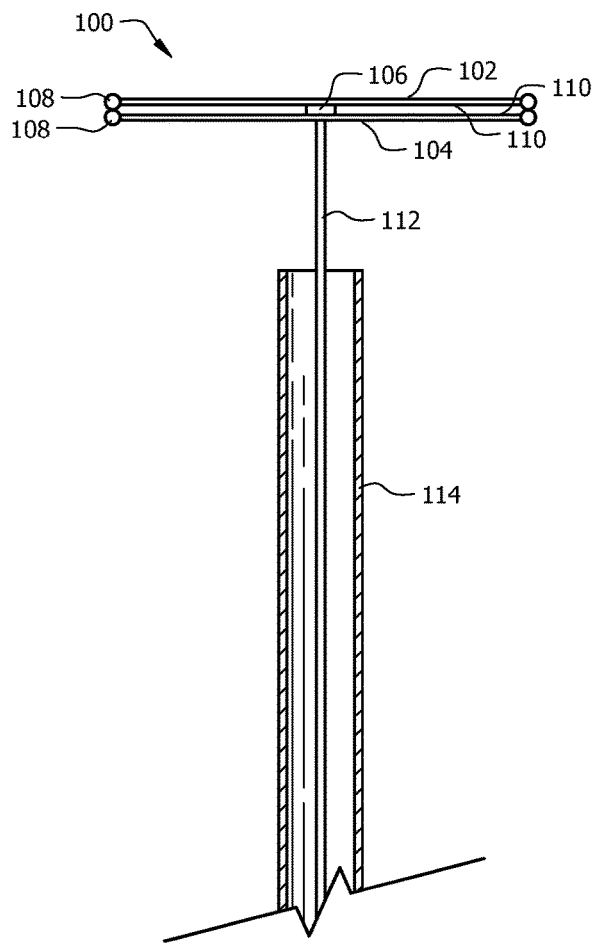
FIG. 1D is a cross-section of the preferred embodiment of the present disclosure in a non-collapsed state and attached to a delivery wire.
Figure 1E:
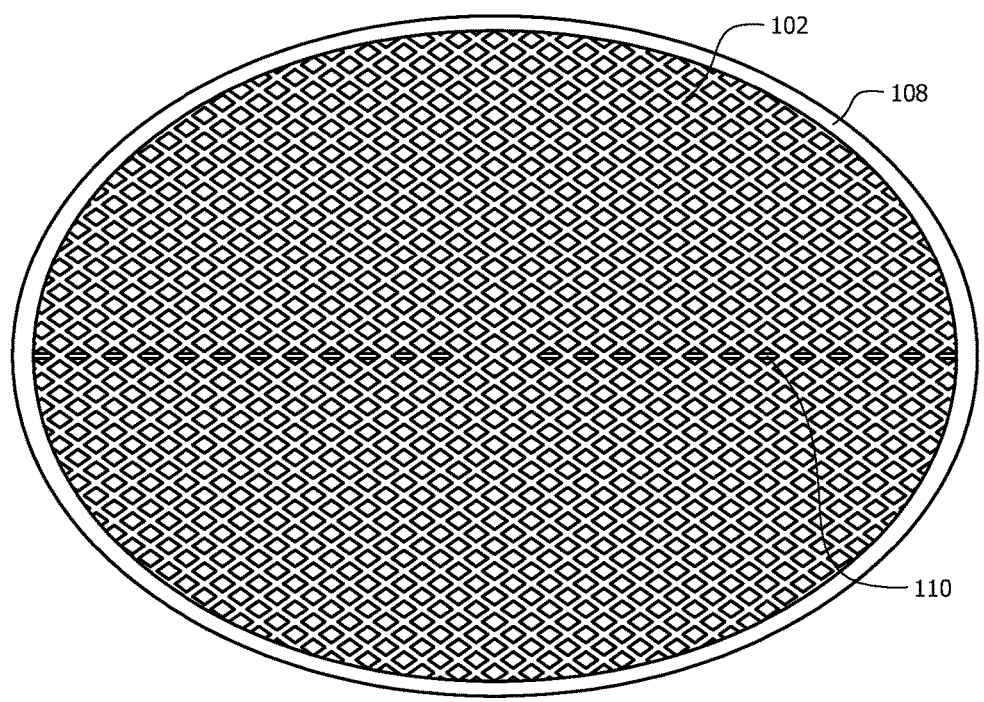
FIG. 1E is a top view of the preferred embodiment of the present disclosure in a non-collapsed state.

FIGS. 1C and 1D show the endovascular clip 100 is in its original configuration, and FIGS. 1A and 1B show the endovascular clip 100 is in the deformed configuration. As shown, the deformed configuration of the self-expanding members 102 and 104 are generally perpendicular to the original configuration of the self-expanding members 102 and 104.

Referring to FIGS. 1A-1D, the two self-expanding members 102 and 104 are connected to each other by the connecting joint 106 disposed between the self expanding members 102 and 104. The connecting joint 106 can be made of any desired material or combination of materials, including, but not limited to, a metal, an alloy, a composite, a polymer, and the like. In one embodiment, the connecting joint 106 may be formed from the same material, e.g., nitinol, as that of the self-expanding members 102 and 104, such that a portion of the mesh of at least one self-expanding member 102 or 104, and/or reinforcing wire 110 (discussed further below), is integral with a portion of the connecting joint 106. Alternatively, the self-expanding members 102 and 104 may be welded to the connecting joint 106. In other embodiments, the self-expanding members 102 and 104 may be attached to connecting joint 106 through appropriate means. In another embodiment, the connecting joint 106 can comprise a radiopaque material. Due to the superelastic properties of the mesh of self-expanding members 102 and 104, the integrity of the material attachment sites between the self-expanding members 102 and 104 and the connecting joint 106 are preferably minimally affected by the folding and unfolding of the self-expanding members 102 and 104 during their transition between the original and deformed conditions.

In one embodiment, the connecting joint 106 has a diameter between about 0.1-2 mm. Referring to FIGS. 1A-1D, the connecting joint 106 preferably should have a diameter that is as small as possible but still sufficient to allow delivery wire 112 to attach to connecting joint 106 and deliver clip 100 to the desired location in the patient. Accordingly, in another embodiment, the diameter of the connecting joint 106 is slightly larger than the diameter of the delivery wire 112. The delivery wire 112 may be attached to the proximal surface of the connecting joint 106 by various means that allow the user to selectively release the connecting joint 106 from the delivery wire 112 known to those skilled in the art. For example, suitable release mechanisms may include mechanical, chemical, electrolytic, temperature-sensitive, remotely-triggered, or other type of release means. One exemplary mechanical release mechanism is a ball mount.

Figure 5A:
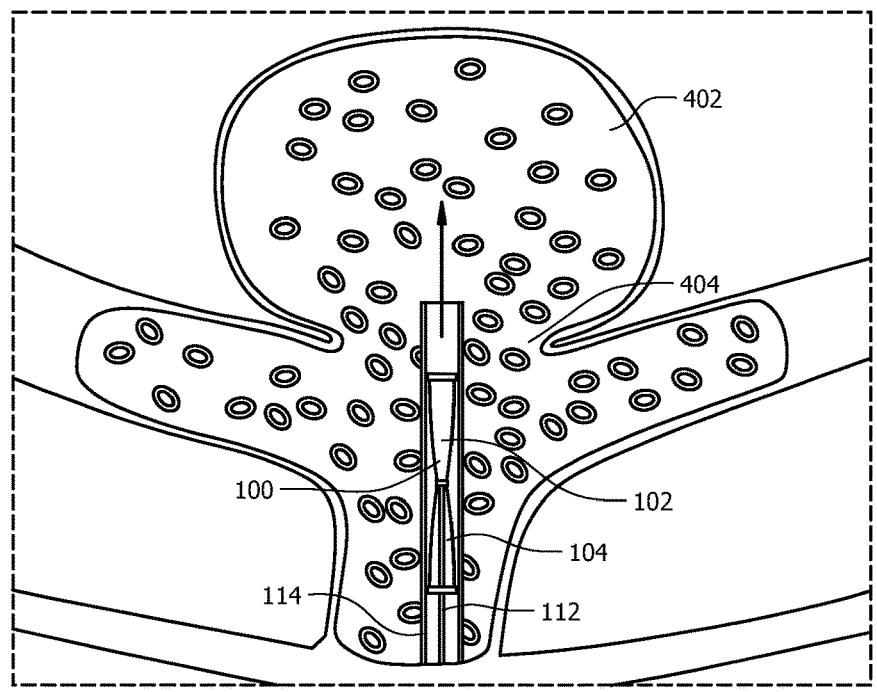
FIG. 5A is a side view of the preferred embodiment of the present disclosure in a collapsed state being inserted into the aneurysm of FIG. 4.
Figure 5B:
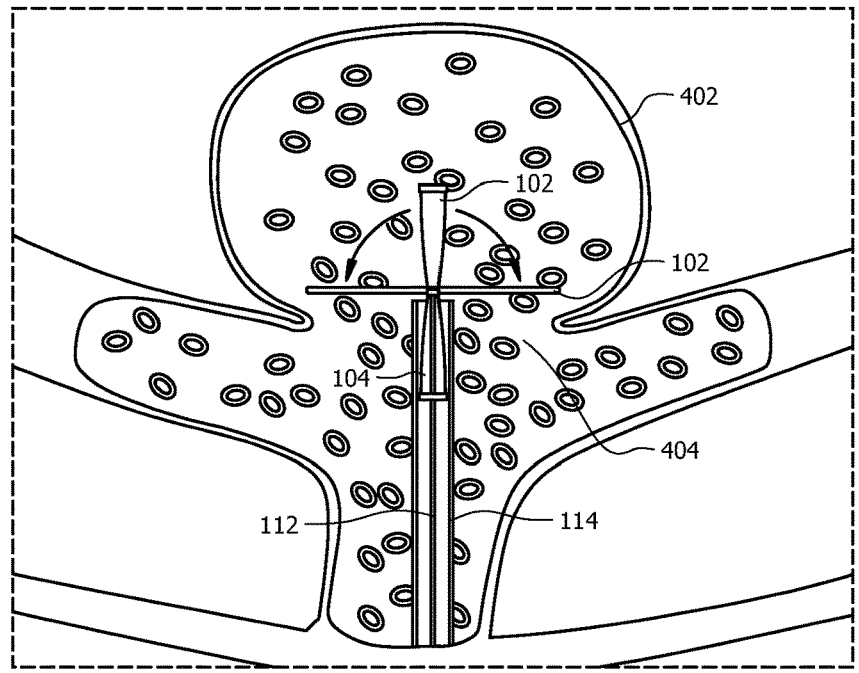
FIG. 5B is a side view of the preferred embodiment of the present disclosure partially deployed from a catheter into a non-collapsed state within the aneurysm of FIG. 4.

The height of the joint 106 and angle and location of attachment of the self expanding members 102 and 104 to the connecting joint 106 are configured to keep the self expanding members 102 and 104 in close parallel proximity, where they are preferably touching one another. In the preferred embodiment, the opposing surfaces, whether the mesh surface and/or frame surface, of the self expanding members 102 and 104 are configured to gently press against each other. This allows for at least the edge of self-expanding members 102 and 104 to slightly squeeze and attach to the neck of the aneurysm when the self-expanding members 102 and 104 have recovered to its original horizontal position, such as that shown in FIGS. 5E and 5F. As shown in FIGS. 5E and 5F, self-expanding members 102 and 104 extend across an opening in the vascular wall in its original configuration once expanded. In one embodiment, the endovascular clip 100 is anchored at the desired location by the slight squeeze and attachment of the self-expanding members 102 and 104. In other embodiments, it is envisioned that other anchoring means, such as additional leg support structures, may be used to supplement the attachment of the self-expanding members 102 and 104 to the neck of the aneurysm or around an opening in the vascular wall.

In one embodiment, the mesh of at least one self-expanding member, 102 or 104, can further be reinforced by a reinforcing wire 110. Referring to FIGS. 1A, 1B, and 1D, in a preferred embodiment, the reinforcing wire 110 is connected at both ends to the peripheral frame 108. The central portion of the reinforcing wire 110 is attached to the connecting joint 106. The substantial portion of the length of the reinforcing wire 110 is attached to the surface of certain strands of the mesh of the respective self-expanding member, 102 or 104. The reinforcing wire 110 may also made of superelastic and/or self-expanding material, such as memory-shaped heated alloy, e.g., nitinol. As discussed above, the reinforcing wire 100 may be formed from the same material as that of the self-expanding members 102 and 104 and connecting joint 106 such that at least a portion of each of these components may be integral with one another. In one embodiment, the reinforcing wire 110 may have a larger diameter than the strands of the mesh. Preferably, the diameter of the reinforcing wire 110 is between about 10-500 microns, and more preferably a diameter of about 50-75 microns. In another embodiment, both self-expanding discs 102 and 104 includes at least one reinforcing wire 110. In embodiments where one or both self-expanding members 102 and 104 include(s) more than one reinforcing wires 110, the wires may be placed to evenly divide the surface of the respective self-expanding disc. For instance, if there are two reinforcing wires 110 for one self-expanding members, they may be placed perpendicular to one another with the intersection being at or near connecting joint 106.

When the clip 100 is in its compressed or deformed state, it is constrained inside the delivery catheter 114. Referring to FIG. 1B, in embodiments having at least one reinforcing wire for each self-expanding member, the reinforcing wires 110 are folded up in a generally longitudinal fashion proximate to the catheter shaft. Referring to FIGS. 5B-5E, once the self-expanding members, e.g. 102, of clip 100 are deployed out of the distal end of the catheter 114, the reinforcing wires 110 move into their biased or original alignment toward each other, thereby bringing the mesh and/or the peripheral frame 108 of each self-expanding member, 102 or 104, toward one another and into a horizontal position.

Alternatively, in an embodiment without reinforcing wire 110, this biased alignment can be otherwise achieved without the need for a central reinforcing wire 110. For instance, in one embodiment, the biased or unconstrained horizontal alignment of the self-expanding members 102 and 104 can be achieved by having some strands of the mesh that are slightly thicker to impart additional strength to the self-expanding member. The thicker wires impart greater strength without significantly increasing the delivery profile of clip 100 while the thinner wires offer support while providing the desired strand density for the mesh and without requiring additional material or increasing the delivery profile. Various permutations are available where in some embodiments, both or one of the self-expanding members 102 and 104 can be without a frame 108 and/or reinforcing wire 110. The different thickness or density arrangements of the strands of each of the self-expanding members 102 and 104 can be adjusted to optimize the member's recovery to the horizontal biased position as described.

The self-expanding members 102 and 104 are configured with desired deployment characteristics and configured to provide sufficient flexibility for tracking through a possibly tortuous vascular system of an individual, such as the intracranial vascular system. The clip 100 may be inserted into a blood vessel in any suitable manner, such as through the use of endovascular, percutaneous, or other minimally invasive surgical techniques. They may be formed in any desired manner, including, but not limited to, braiding, welding, molding, weaving, laser-cutting a tube or sheet, and the like.

The number of wires, braid angle, pore size, profile, diameter, shape etc. of the mesh of the self expanding members 102 and 104 can vary depending on the application. For instance, a larger expanding member configured for a larger size aneurysm may have more wires than a smaller member. As mentioned above, the circumference of the self expanding members 102 and 104 can have of any suitable shape (e.g., oval, square, etc). In addition, the self-expanding members 102 and 104 can also have three-dimensional characteristics, including but not limited to, flat or generally even, conical, convex, concave, or any other shape depending on the application. Preferably, the shapes of the circumference and three-dimensional characteristics of both self-expanding members 102 and 104 are the same.

In one embodiment, the diameter of the self-expanding members can be between about 2-20 mm, and preferably about 5-7 mm. In the preferred embodiment, the diameter of the self-expanding members 102 and 104 are determined at least by the size of the aneurysm. In particular, the diameter of the self-expanding members 102 and 104 is preferably about 1-2 mm larger than the neck of the target aneurysm. The density of the wire mesh of the self-expanding members 102 and 104 can affect the performance of the clip 100 in isolating the target aneurysm from incoming blood flow. In the preferred embodiment, the self-expanding members 102 and 104 have high density of wires forming the mesh to reduce blood flow across the self expanding members 102 and 104 and into the aneurysm.

Figure 2A:
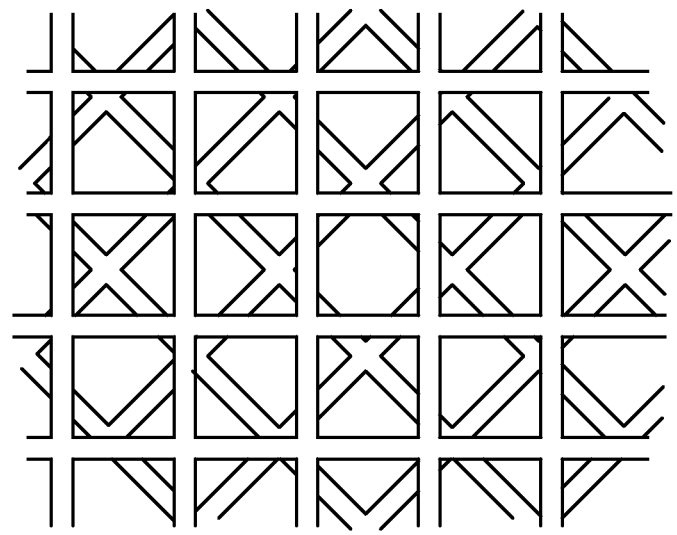
FIG. 2A illustrates an exemplary configuration of the wire mesh arrangement of the preferred embodiment of the present disclosure.
Figure 2B:
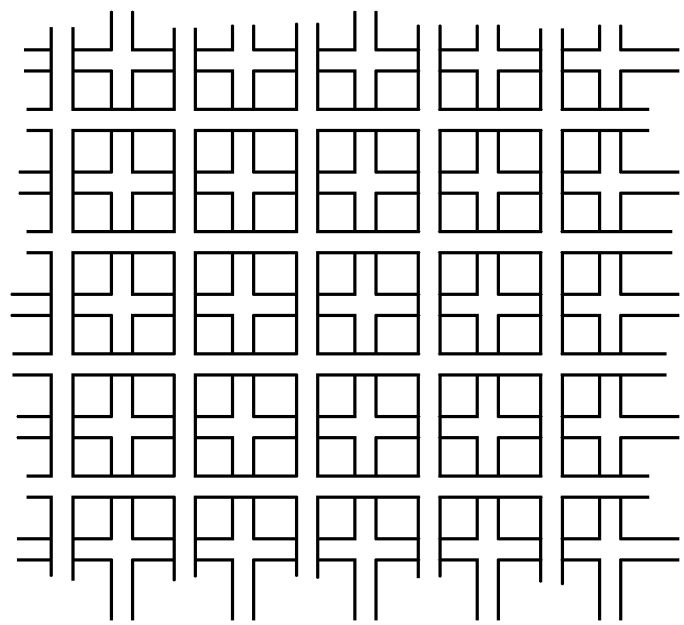
FIG. 2B illustrates another exemplary configuration of the wire mesh arrangement of the preferred embodiment of the present disclosure.

Referring to FIG. 2, additionally, the alignment of the opposing interstices and strands of the wire mesh of each self expanding members 102 and 104 can be offset against one another such that the wires or intersections of one mesh fully or partially obstructs the pores of the other mesh. FIGS. 2A and 2B show two exemplary embodiments of such offset configurations. As shown, the strands of each mesh are inter-positioned so that the spaces between them are substantially blocked. This will further increase the density of the mesh of the self expanding members 102 and 104 and decrease the size of these pores. In embodiments where the self-expanding disc may contain more than one layer of mesh, each mesh may be positioned as described to provide further blocking of the openings. As such, the off-set arrangement of the mesh of the self-expanding members increases the blocking effect of the self expanding members 102 and 104 with respect to the blood flow to the aneurysm. In another embodiment, the arrangement and size of the strands are configured to allow substantial or complete obstruction of the interstices.

Figure 2C:
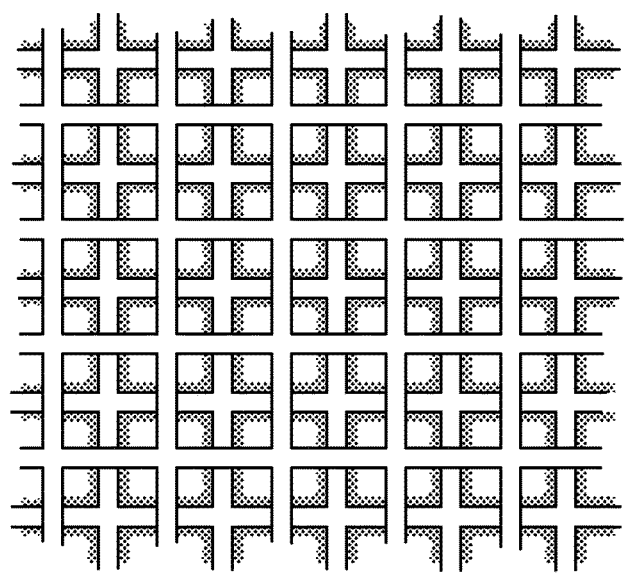
FIG. 2C illustrates a further exemplary configuration of the wire mesh arrangement of the preferred embodiment of the present disclosure.

Additionally, referring to FIG. 2C, at least one mesh of either self expanding member 102 or 104 can be coated with a material designed to produce the desired effect of obstructing the openings of the mesh. In the preferred embodiment, the distal self expanding member 102 (or bottom mesh in FIG. 2C) that is placed inside the aneurysm has this coating. Such coating of at least some of the strands can include a swellable material that expands in volume when it comes in contact with a liquid or exposure to heat. An example of the swellable material includes, but are not limited to, a hydrogel or hydrogel foam. The swellable gel material can expand in volume as a result of hydration of it molecular structure, or by the filling of its pores with liquid (blood), or both.

The enlargement of the swellable coating or composition is designed to fill and close any remaining openings in the interstices of the mesh of self expanding members 102 and/or 104. Accordingly, the neck of the aneurysm can be completely sealed with the clip 100 inserted in place, thereby blocking the blood flow into the aneurysm with the resultant aneurysm thrombosis. In one embodiment, the mesh of clip 100 may be less dense, i.e., less wires, than other clips that are not coated with the expandable coating. That is, the addition of the expansible material allows a clip 100 to perform the same function with less metallic wires, thereby providing a device with a lower profile for easier delivery to the aneurysm.

Suitable swellable materials include, but are not limited to: hydrogels; hydrophilic polymers with or without conjugated collagen as described in U.S. Pat. No. 5,413,791, the disclosure of which is incorporated by reference. In particular, conjugated collagen can include biocompatible, macroporous, hydrophobic hydrogel foams; and compressible, non-hydrophobic polymeric foam materials, such as polyurethane. A particularly preferred foam includes a water-swellable foam matrix formed as a macroporous solid comprising a foam stabilizing agent and a polymer or copolymer of a free radical polymerizable hydrophobic olefin monomer cross-linked as described in detail in U.S. Pat. Nos. 5,570,585 and 6,500,190, the disclosures of which are incorporated by reference.

Another suitable swellable material is a porous hydrated polyvinyl alcohol foam (PAF) gel prepared from a polyvinyl alcohol solution in a mixed solvent consisting of water and a water-miscible organic solvent, as described, for example, in U.S. Pat. No. 4,663,358, the disclosure of which is incorporated by reference.

Figure 3:
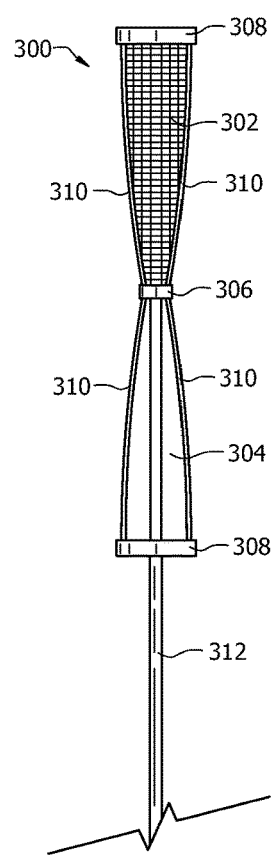
FIG. 3 is a side view of another embodiment of the present disclosure in a collapsed state.

Referring to FIG. 3, according to another aspect of the present disclosure, the swellable material coated on one lattice, preferably the distal lattice, forms a sufficient barrier to prevent further blood flow into the aneurysm and promote healing such that a second lattice is not necessary. As shown by FIG. 3, endovascular clip 300 is similar to clip 100 of FIGS. 1A-1E, except the distal self-expanding disc 302 includes a lattice and proximal self-expanding disc 304 includes only reinforcing wire 310 and frame 308. The frame 308 of the proximal self-expanding disc 304 slightly presses against frame 308 of distal self-expanding disc 302 to anchor clip 300 to the neck of an aneurysm while the lattice of the proximal self-expanding disc 304, having its interstices closed by the swellable material, serves as the barrier. The reinforcing wire 310 of the proximal self-expanding member 304 provides support and connects the frame 308 of the proximal self-expanding member 304 to the joint 306. This aspect of the present disclosure allows for clips that are lighter and require less material to make. In other embodiments, the distal self-expanding disc 302 need not include frame 308 and/or reinforcing wire 310 as discussed above with respect to clip 100. The clip 300 may be anchored to the neck of the aneurysm by the pressure between frame 308 of the proximal self-expanding member 304 and the lattice of the distal self-expanding disc 302, where the diameter and/or density of the lattice strands close to the peripheral distal self-expanding disc 302 are greater than that of the strands closer to the center. Joint 316 functions similarly to joint 106 and allows for releasable engagement with delivery wire 312. Other features discussed herein with respect to clip 100, such as dimensions, materials, strand density, strand diameter, shape of the self-expanding members, etc., are also applicable to clip 300.

In other embodiments, the mesh of self-expanding members 102 and 104 may be further coated or alternatively coated with additional materials, such as bioactive material which promote cell growth and attachment. The bioactive material may also be thrombogenic. Examples of the bioactive material include, but are not limited to, materials that increase cell attachment and/or thrombogenicity include both natural and synthetic compounds, e.g. collagen, fibrinogen, vitronectin, other plasma proteins, growth factors (e.g. vascular endothelial growth factor, "vEGF"), synthetic peptides of these and other proteins or peptides having attached RGD (arginine glycine-aspartic acid) residues, generally at one of both termini or other cell adhesion peptides, i.e., GRGDY, oligonucleotides, full or partial DNA constructs, natural or synthetic phospholipids or polymers with phosphorylcholine functionality.

In yet another embodiment, the self expanding members 102 and 104 may be at least partially adapted to elute a pharmaceutical agent. The pharmaceutical agent can produce several biologic effect including but not limited to promotion of cell growth and attachment. As used herein, "eluting" includes, but not limited to, the following releasing, leaching, diffusing, or otherwise providing a pharmaceutical agent to a target area. Accordingly, the embodiments of the present disclosure allow for accurate delivery of the bioactive material and/or pharmaceutical agent to the aneurysm sac with minimal risks of migration of these material out of the aneurysm and into the parent vessel, where such migration would pose significant health risks to a patient.

Referring to FIGS. 1A-5D, clip 100 is inserted and moved to the aneurysm through the delivery catheter 114, which has proximal and distal catheter ends separated by a hollow catheter lumen preferably a cylindrical shaft. The distal end of catheter 114 is adapted for placement within the blood vessel inside an aneurysm sac. The clip 100 and delivery wire 112 fits within the lumen of the catheter 114.

Referring to FIGS. 1A-1D, the delivery wire 112 is releasably connected to the proximal surface of the connecting joint 106. As discussed above, the various suitable means known to those skilled in the art include mechanical, chemical, electrolytic, temperature-sensitive, remotely-triggered, or other type of release means. In one embodiment, the delivery wire 112 is oriented substantially perpendicularly to the horizontal axis of the self expanding members 102 and 104. Alternatively, it can be oriented in variable angulated fashion relative to the horizontal axis of the self expanding members 102 and 104. The delivery wire 112 allows for various movements of the self expanding members 102 and 104 in relation to the catheter 114 or in relation to the neck of the aneurysm. In one embodiment, when affixed, the delivery wire 112 can facilitate minor changes in the position of the self expanding members 102 and 104 during use. Also, the delivery wire 112 can also increase positional stability of the self expanding members 102 and 104.

The body of the delivery wire 112 has a length sufficient to extend through the vascular system of the patient to place the clip 100 in the desired deployment location. In one embodiment, the delivery wire 112 has a length of between about 50 cm-250 cm, more preferably a length of about 125-175 cm. The diameter of the delivery wire 112 may be constant or may vary along the length of the delivery wire 112. For example, the diameter of the delivery wire 112 toward the proximal end away from the patient may be between about 0.2-1 mm, and preferably about 0.3-0.4 mm, while the diameter near the distal operative end may be between about 0.05-1 mm, and more preferably about 0.1-0.2 mm. Accordingly, the diameter of the delivery wire 112 may taper from the proximal end to the distal end.

In one embodiment, the expandable clip 100 may include at least one radiopaque portion to facilitate visualization using, for example, one or more of fluoroscopy, computer tomography (CT) fluoroscopy, or the like. The radiopaque portion can be a component of the expandable clip 100. In one embodiment, the connecting joint 106 comprises the radiopaque portion. The radiopaque material can include platinum or tantalum DFT Nitinol or could be a separate radiopaque marker and/or material attached to or coated on at least a portion of the expandable member.

Figure 4:
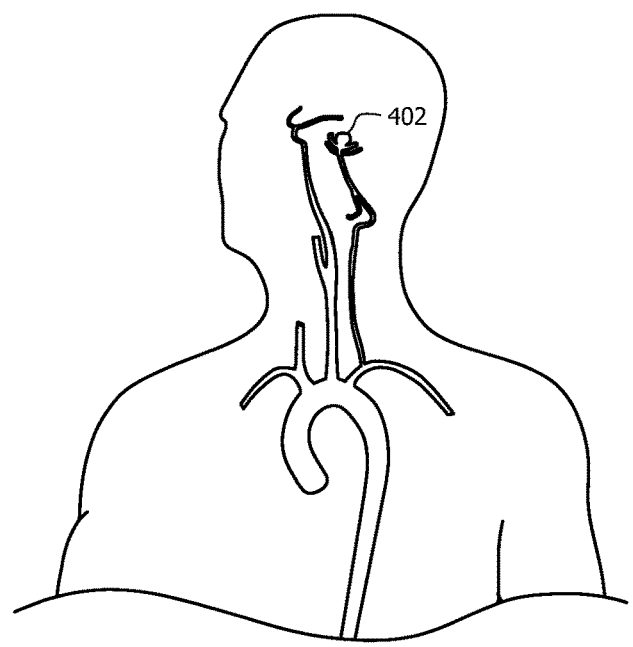
FIG. 4 illustrates a patient with a brain aneurysm to be treated with one embodiment of the present disclosure.

According to another aspect of the present disclosure, there is a method of treating an aneurysm, particularly a brain aneurysm 402 of FIG. 4, using the endovascular clips of the present disclosure, such as clip 100 or clip 300. While the disclosure may refer to numerical components of clip 100, it is understood that the discussion is applicable to clip 300 and its components. In one embodiment, an angiographic evaluation of the aneurysm is performed. Based on the anatomical data obtained, namely the measurements of the aneurysm neck dimensions in several planes, the shape and configuration of the aneurysm neck, the shape and branching pattern of the parent vessels, and the angle of attachment of the aneurysm to the parent vessels, a suitable clip 100 is selected. Referring to FIG. 1, in one embodiment, the anatomical data provides the shape of the circumference of self-expanding members 102 and 104, as well as the diameter, three-dimensional properties (e.g., concave, convex, flat), thickness, etc.

For instance, referring to FIG. 4, aneurysm 402 is generally known as a bifurcation aneurysm, which is often difficult to treat with conventional means, such as coils and stents, due to the "T" configuration of the main artery. For this type of aneurysm, a clip 100 with concave self-expanding members 102 and 104 may be the most appropriate. On the other hand, for a side wall aneurysm, a clip 100 with flat self-expanding members 102 and 104 may be more appropriate. Also, an aneurysm that is relatively smaller may benefit from a clip with only one lattice, such as clip 300. While FIG. 4 shows a bifurcation aneurysm in the brain, the embodiments of the present disclosure are applicable to other types of aneurysm occurring elsewhere in the body.

Referring to FIG. 5, in one embodiment, the size of the self expanding members 102 and 104 of clip 100 is slightly larger than the neck 404 of the aneurysm 402. Preferably, the diameter of the self expanding members 102 and 104 is about 0.5 to 3 mm larger than the diameter of the neck, and more preferably about 1-2 mm larger. The slightly larger size allows the clip 100 to substantially or completely cover the neck of the aneurysm when the self expanding members 102 and 104 are fully deployed proximally and distally.

In another embodiment, a suitable shape of the self expanding members 102 and 104 is selected to conform to the anatomy of the aneurysm and parent vessel without significant deformation or stress on the walls of either the aneurysm or the vessel.

In one embodiment, under life fluoroscopic imaging the delivery catheter is advanced over a wire to a position just inside the aneurysm sac. Referring to FIG. 5A, the selected clip 100 is loaded inside the proximal end of the catheter, where the clip 100 is longitudinally folded and constrained in the collapsed condition inside the lumen of catheter 114. Referring to FIGS. 5A and 5B, using a detachable delivery wire 112, the clip 100 is pushed distally through the catheter lumen until the distal self expanding member 102 is pushed beyond the distal end of the catheter 114 and into aneurysm 402. At this point, the expanding member 102 is fully released from the catheter 112 and expanded within the interior of the aneurysm 402 to its biased shape. In embodiments having some superelastic material such as nitinol, the expansion is partially due to exposure to an activation mechanism such as temperature beyond the threshold temperature.

Figure 5C:
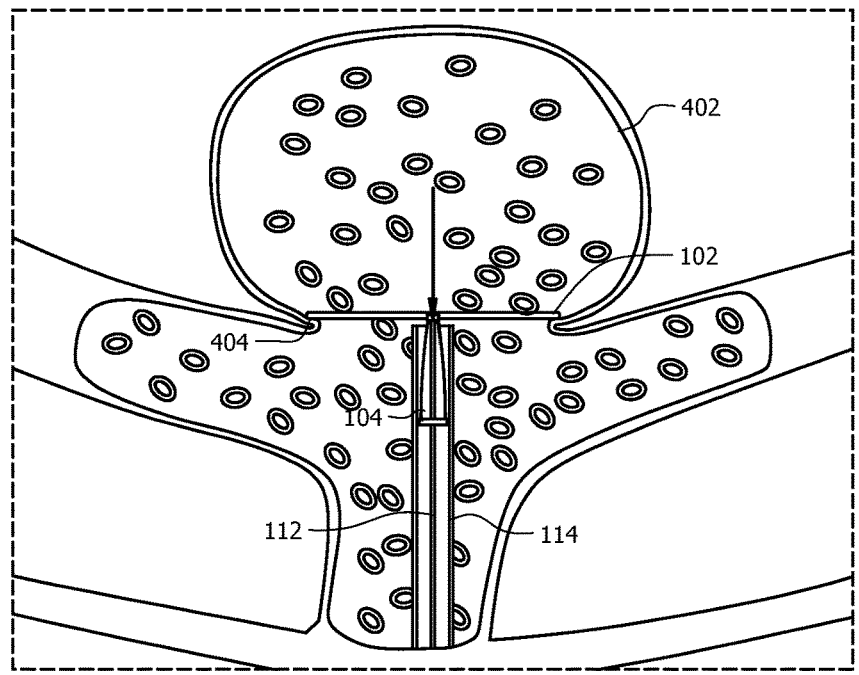
FIG. 5C is a side view of the preferred embodiment of the present disclosure in a non-collapsed state at the neck of the aneurysm of FIG. 4.
Figure 5D:
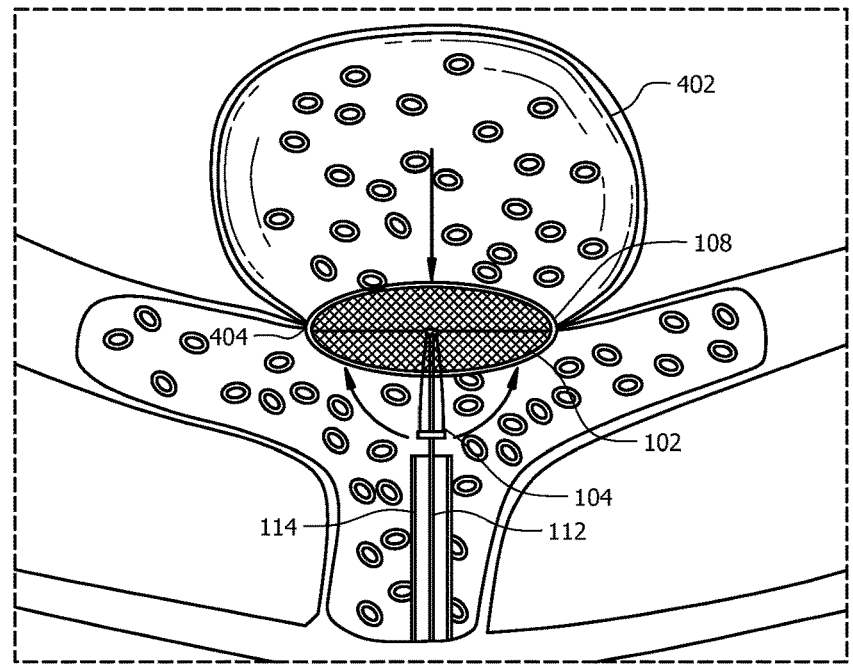
FIG. 5D is a perspective view of the preferred embodiment of the present disclosure in a non-collapsed state at the neck of the aneurysm of FIG. 4.
Figure 5E:
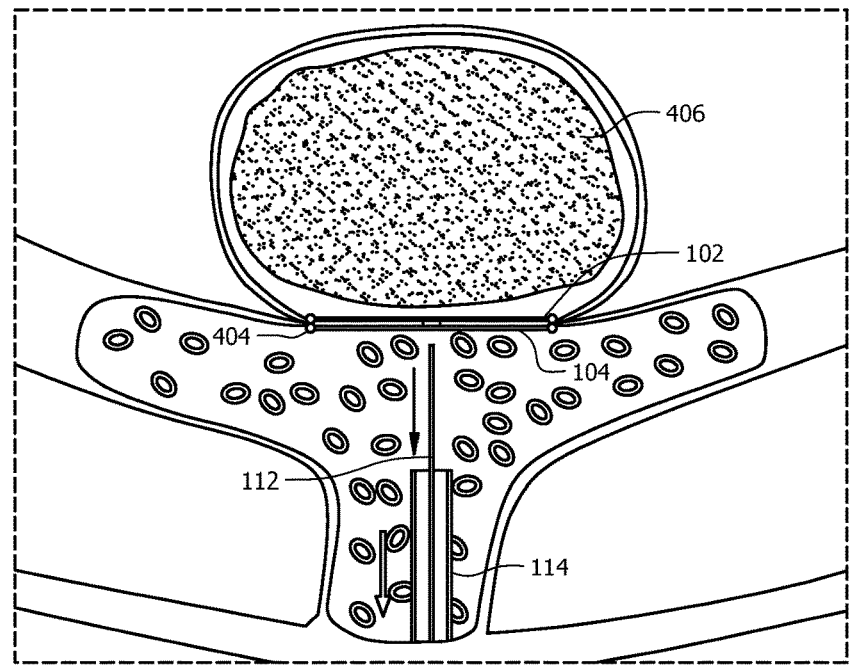
FIG. 5E is a side view of the delivery wire detaching from the preferred embodiment of the present disclosure completely deployed in a non-collapsed state.
Figure 5F:
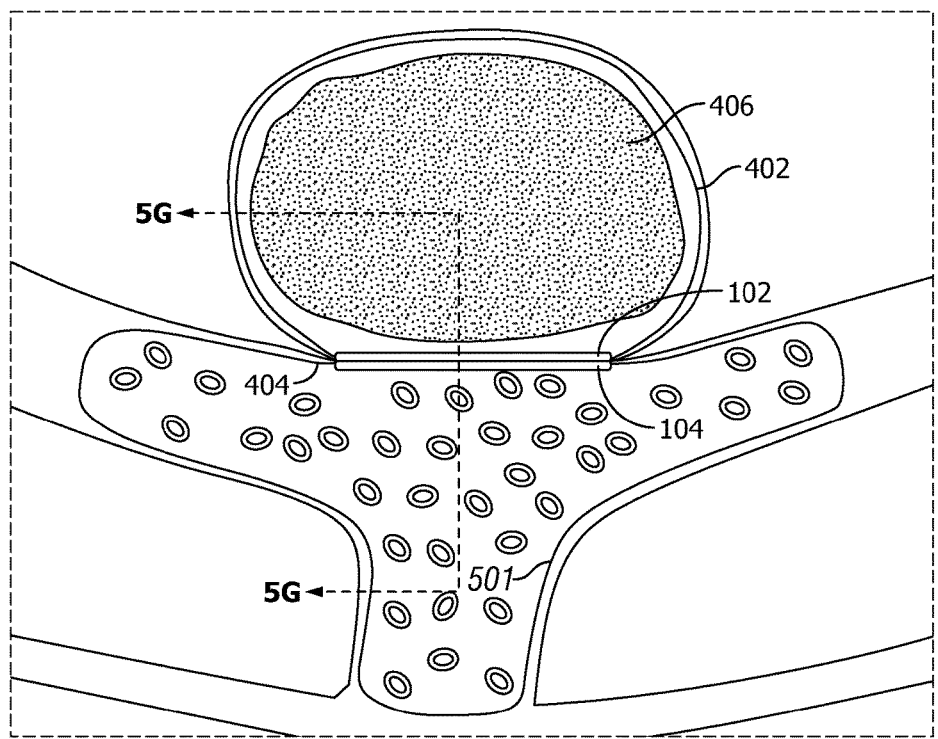
FIG. 5F is a side view of the aneurysm of FIG. 4 treated with the preferred embodiment of the present disclosure.

In one embodiment, referring to FIG. 5C, the distal member 102 is then pulled toward the neck 404 so that it touches the inside walls of the aneurysm neck 404. While stabilizing the distal member 102 in position by holding the delivery wire 112 in place, the catheter 114 may be slowly retracted to uncover the proximal self expanding member 104 outside the aneurysm neck. Referring to FIG. 5D, at this point, the proximal self expanding member 104 is fully released from the catheter 114 and deploys to its biased shape. Referring to FIGS. 5D-5F, the self expanding member 104 also moves toward the distal self expanding member 102, thereby clinching the neck 404 of the aneurysm between the two members 102 and 104.

In one embodiment, referring to FIG. 2, the framed wire segments or mesh of the self expanding members 102 and 104 are inter positioned so that the spaces between the wires are substantially blocked. Referring to FIGS. 5E and 5F, after the self expanding members 102 and 104 are fully deployed and positioned at the neck 404 of aneurysm 402, the delivery wire 112 is detached from the joint 106 and removed from the body of the patient. Once attached, the clip 100 impede further flow into the aneurysm from the artery by the density and arrangement of the mesh of the self-expanding members 102 and 104 where the openings of one mesh is covered with the strands of another mesh. The obstruction of the interstices can be further supported by the configuration of the self-expanding members 102 and 104 slightly pressing against one another. In embodiments using clip 300 of FIG. 3, the lattice of one self-expanding member is sufficient to serve as the barrier.

Referring to FIGS. 2C, 3, 5E, and 5F, in embodiments where the mesh of at least one self expanding member, preferably distal member 102, is coated with a swellable material, the swellable material reacts either at the presence of fluid and/or higher temperature, such as vascular content, and swells up to seal any remaining opening of the self expanding members 102 and 104. In one embodiment, the swellable material and arrangement of the mesh of the self expanding members 102 and 104 completely seals the neck of the aneurysm and block the blood flow into the aneurysm with the resultant aneurysm thrombosis, i.e., formation of clot 406, and occlusion of the aneurysm. The swellable material may be activated by an external stimuli instead of or in addition to being exposed to a fluid and/or higher temperature. One example of an external stimuli is applying an electrical current to the endovascular clip 100.

Figure 5G:
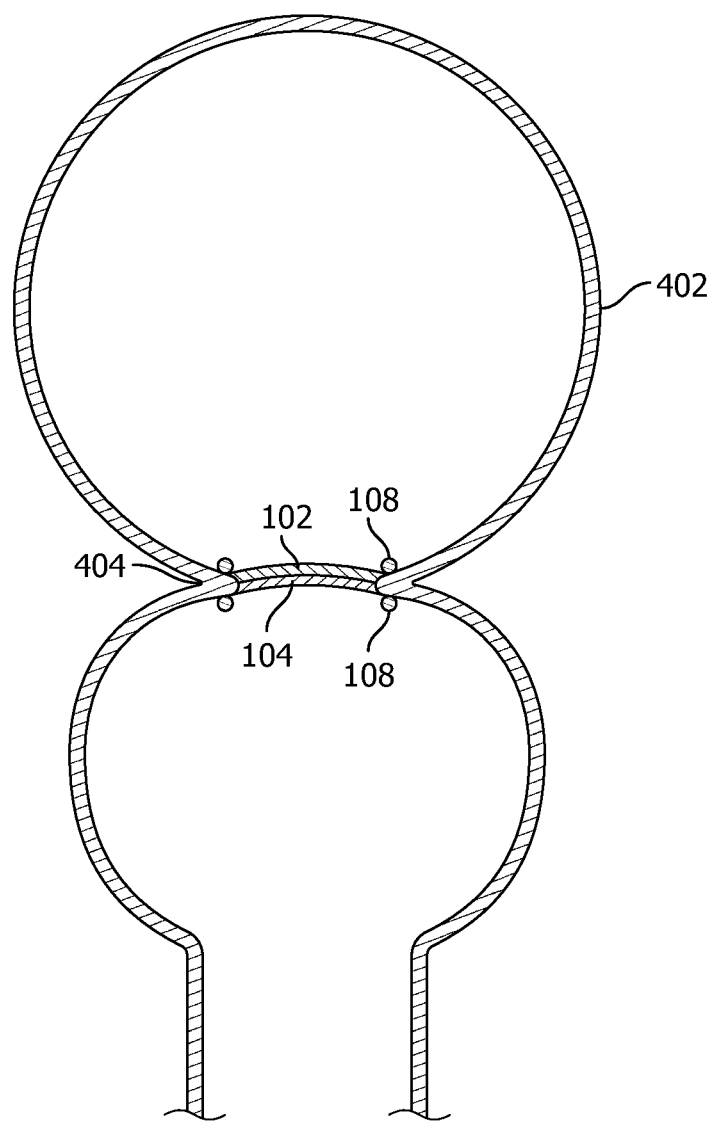
FIG. 5G illustrates a cross sectional view side view of the vascular structure illustrated in FIG. 5F to show the 3D shape of the proximal position of the two lattice structures.

"FIG. 5G is a cross sectional view of the vessel 501 showing the proximal 104 and distal 102 lattice having an arch or concave shape consistent with the shape of the vessel wall. The self-expanding members 102 and 104 can have three-dimensional characteristics, including but not limited to flat or generally even, conical, convex concave, or any other shape depending on the application. Also illustrated is the neck 404 of the aneurysm 402 and the frames 108 of each lattice."

In another embodiment, the mesh of at least one expanding member, preferably the distal self-expanding member 104, is further coated with the bioactive material or eluting drugs as described above. In these embodiments, the bioactive material or eluting drugs can further accelerate occlusion and healing of the aneurysm by inducing thrombosis and scar formation as well as stimulation of the lining of the vessel to grow on and cover the disc with the disc acting as a scaffolding upon which the cells grow which also lead to complete sealing the neck of the aneurysm and block the blood flow into the aneurysm with the resultant aneurysm thrombosis i.e., formation of clot 406 and closure. The healing of the aneurysm is achieved at east by the bioactive material or eluting drugs stimulating the healing of the lining of the blood vessel 501, which leads to encapsulation of the aneurysm.

As shown, the embodiments of the present disclosure allows for treatment of difficult aneurysms, such as a bifurcation aneurysm in the brain. In addition, the embodiments of the present disclosure also allows for delivery of materials, such as the bioactive materials and eluting drugs described above, to specific locations in the body to treat that particular site. In comparison, prior methods do not provide precise delivery of these materials, which expose the patient to significant risks because these bioactive materials and eluting drugs are dangerous if they are not delivered to the targeted location.

Although the embodiments of the present disclosure and their advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. An aneurysm occlusion and healing device comprising:
   (a) a distal member in an original configuration, comprised of a frame-less two-dimensional mesh of intersecting and interposed wires configured to be placed inside an aneurysm and extend across an aneurysm junction with the blood vessel to form a barrier to blood flow into the aneurysm;
   (b) the mesh of the distal member is configured to adhere to inner lining of the aneurysm junction with the blood vessel, where intersected and interposed wires of the distal member form a scaffold to allow endothelium to grow on a surface of the distal member for sealing and healing of the aneurysm;
   (c) a mesh-less proximal member, comprised of one or more support wires radially configured to be placed outside the aneurysm extending across an aneurysm neck and vessel wall and to press against the opposing surface of the distal member and adjacent vessel walls to maintain the tight adherence of the distal member against the neck of the aneurysm;
   (d) where each of the distal and proximal members have an original configuration and a deformed configuration;
   (e) wherein said deformed configurations are configured to change to said original configurations by an activating mechanism; and
   (f) wherein a portion of each of said distal and proximal members are attached to a joint component.

2. The endovascular clip of claim 1 wherein at least one of the distal and proximal members comprises nitinol.

3. The endovascular clip of claim 1 wherein said activating mechanism comprises a temperature above a defined threshold.

4. The endovascular clip of claim 1 wherein said mesh further comprises a swellable material configured to expand in volume upon exposure to an activating condition.

5. The endovascular clip of claim 4 wherein said swellable material is selected from the group consisting of hydrogel, hydrogel foam, hydrophilic polymers with conjugate collagen, hydrophilic polymers without conjugated collagen, porous hydrated polyvinyl alcohol foam (PAF) gel, and any combination thereof.

6. The endovascular clip of claim 5 wherein said swellable material seals at least a portion of said interstices of the respective deformable component when the swellable material is exposed to vascular content.

7. The endovascular clip of claim 1 wherein said mesh further comprises a bioactive material configured to promote cell growth.

8. The endovascular clip of claim 7 wherein said bioactive material comprises a thrombogenic material.

9. The endovascular clip of claim 1 wherein said joint component is configured to be releasably attached to a delivery wire.

10. The endovascular clip of claim 1 wherein a portion of vascular wall at the aneurysm neck is sandwiched between a portion of said distal member and a portion of said proximal member when said distal member and proximal member are extended across the opening in the vascular wall.

11. The endovascular clip of claim 1 further comprising a radiopaque material.

12. The endovascular clip of claim 1 wherein said opening in a vascular wall comprise a neck of an aneurysm.

13. The endovascular clip of claim 1 wherein said proximal member comprises a wire.

14. The aneurysm occlusion and healing device of claim 1, wherein the distal member further comprises one or more reinforcing wires.

* * * * *